（12）United States Patent
Khieu et al.

(10) Patent No.: US 9,320,525 B2
(45) Date of Patent: Apr. 26, 2016

(54) OCCLUSION STENT

(75) Inventors: Aaron Khieu, Maple Grove, MN (US);
Daniel James Horn, Shoreview, MN (US); Anthony C. Vrba, Maple Grove, MN (US); John Blix, Maple Grove, MN (US); Kent Harrison, Maple Grove, MN (US); Timothy J. Ley, Shoreview, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1626 days.

(21) Appl. No.: 12/555,891

(22) Filed: Sep. 9, 2009

(65) Prior Publication Data

US 2010/0132718 A1 Jun. 3, 2010

Related U.S. Application Data

(60) Provisional application No. 61/119,576, filed on Dec. 3, 2008.

(51) Int. Cl.
| | |
|---|---|
| *A61F 6/20* | (2006.01) |
| *A61B 17/12* | (2006.01) |
| *A61F 6/22* | (2006.01) |
| *A61F 6/00* | (2006.01) |
| *A61B 17/00* | (2006.01) |

(52) U.S. Cl.
CPC ..... *A61B 17/12022* (2013.01); *A61B 17/12109* (2013.01); *A61B 17/12168* (2013.01); *A61B 17/12172* (2013.01); *A61B 17/12177* (2013.01); *A61F 6/20* (2013.01); *A61F 6/22* (2013.01); *A61F 6/225* (2013.01); *A61B 17/12* (2013.01); *A61B 17/1214* (2013.01); *A61B 17/1215* (2013.01); *A61B 17/12145* (2013.01); *A61B 2017/00867* (2013.01); *A61F 6/00* (2013.01)

(58) Field of Classification Search
CPC ............... A61F 6/00; A61F 6/20; A61F 6/22; A61F 6/225; A61B 17/12; A61B 17/12022; A61B 17/1214; A61B 17/12145; A61B 17/1215; A61B 17/12168; A61B 17/12172; A61B 17/12177; A61B 2017/00867
USPC ................... 128/830, 831, 887; 606/157, 158
See application file for complete search history.

(56) References Cited

U.S. PATENT DOCUMENTS

| | | | |
|---|---|---|---|
| 4,185,618 A | 1/1980 | Corey | |
| 6,579,260 B2 * | 6/2003 | Maki et al. | 604/103.07 |
| 2006/0009798 A1 | 1/2006 | Callister et al. | |
| 2007/0083227 A1 | 4/2007 | Van Der Burg et al. | |
| 2008/0302368 A1 * | 12/2008 | McGuckin et al. | 128/831 |

FOREIGN PATENT DOCUMENTS

| | | |
|---|---|---|
| WO | 2005 / 074844 | 8/2005 |
| WO | 2008 / 024491 | 2/2008 |

* cited by examiner

*Primary Examiner* — Keri J Nelson
(74) *Attorney, Agent, or Firm* — Kacvinsky Daisak Bluni PLLC

(57) ABSTRACT

A device for occluding a target body lumen, comprises a wire structure defining a wire structure lumen extending therethrough and movable between a reduced diameter insertion configuration and an expanded diameter deployed configuration and a basket structure extending across the wire structure lumen and including therein a cell growth promoting agent to promote cell growth across the wire structure lumen to occlude the target body lumen.

18 Claims, 2 Drawing Sheets

OCCLUSION STENT

PRIORITY CLAIM

This application claims the priority to the U.S. Provisional Application Ser. No. 61/119,576, entitled "Occlusion Stent" filed on Dec. 3, 2008. The specification of the above-identified application is incorporated herewith by reference.

BACKGROUND

There are many methods of birth control available to women. However, few of those methods are permanent and those that are permanent require surgical incisions. However, one currently available permanent method of birth control involves the transcervical implantation (i.e., without incision) of a micro-insert device in the fallopian tube to prevent ovum from entering the uterus and to prevent sperm from traveling into the fallopian tube. As no incisions are required, these devices may be implanted without general anesthesia. Once implanted, scar tissue begins to form over coils of the device permanently blocking the fallopian tubes. Micro-insert devices currently on the market comprise a Nitinol outer coil and a stainless steel inner coil with PET fibers wound therearound.

SUMMARY OF INVENTION

The present invention is directed to a device for occluding a target body lumen, comprising a wire structure defining a wire structure lumen extending therethrough and movable between a reduced diameter insertion configuration and an expanded diameter deployed configuration and a basket structure extending across the wire structure lumen and including therein a cell growth promoting agent to promote cell growth across the wire structure lumen to occlude the target body lumen.

DETAILED DESCRIPTION

The present invention, which may be understood with reference to the following description and the appended drawings, relates to devices for occluding body lumens. Exemplary embodiments of the present invention describe devices that maybe implanted into a fallopian tube to provide a permanent method of birth control by preventing ovum from entering the uterus. Specifically, devices according to the present invention include a structure treated with a cell growth promoting agent which, in an operative position, extends across the lumen to be occluded such that a greater inter-luminal surface area is provided for tissue to grow, resulting in a complete blockage of the lumen.

It should be noted, however, that although the embodiments of the present invention are described in regard to the occlusion of the fallopian tube, the present invention may be utilized in any body lumen or vessel that may require permanent occlusion. Those skilled in the art will understand that, although the embodiments detailed below are described in conjunction with implantation procedures which do not require incisions and which are intended to occlude the fallopian tubes, the devices and methods of this invention are applicable to any procedure for permanently occluding a lumen even where that lumen is accessed via an incision. For example, the devices described below may be employed to permanently occlude the vasa deferentia to sterilize a male, to occlude the ductus arteriosus for PDA closures in pediatric cardiology and to facilitate closures to correct arteriovenous (AV) malformations. As described above, known micro-insert devices permit tissue growth around coils thereof, but do not provide a bridge from one side of a fallopian tube to an opposite side permitting tissue to grow quickly within the coils by forming from both sides of each of the fallopian tubes.

Figure 1:
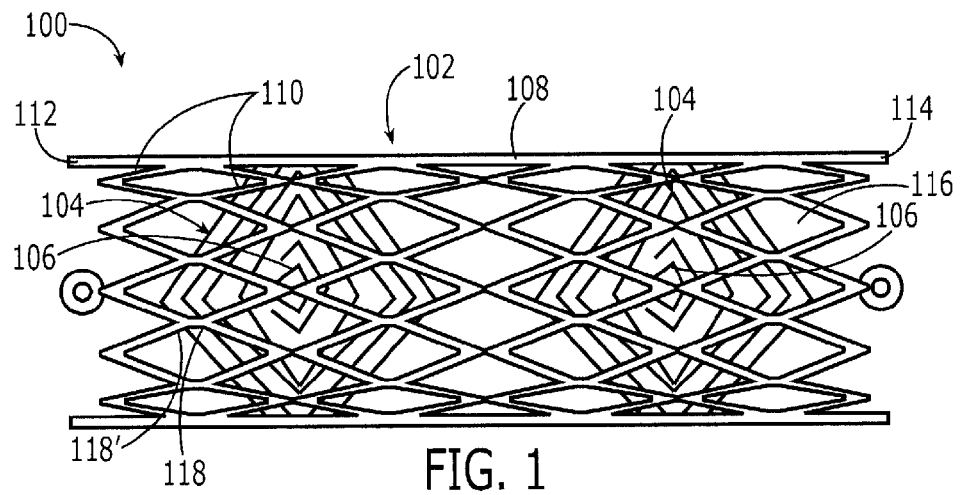
FIG. 1 shows a side view of a device, according to an exemplary embodiment of the present invention, including a cell growth promoter agent in a four-prong basket.
Figure 2:
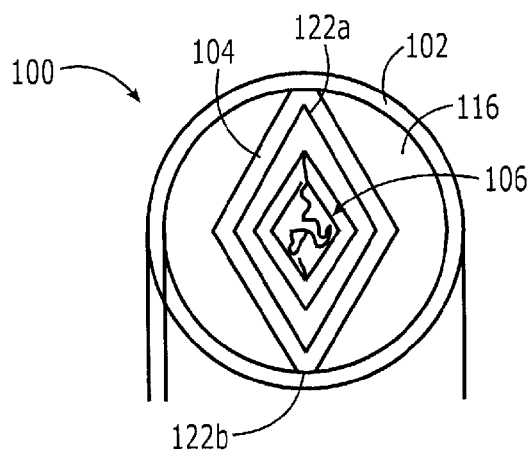
FIG. 2 shows an end view of the device of FIG. 1.

As shown in FIGS. 1-2, a device 100 according to an exemplary embodiment of the invention comprises a stent 102 and a basket structure 104 containing a cell growth promoting agent 106 (e.g., ultra high weight polyethylene fibers, polyester fibers, copper fibers, collagen fibers). The stent 102 extends from a proximal end 112 to a distal end 114 with the basket structure 104 attached to at least one of the proximal and distal ends 112, 114, respectively. The device 100 may be implanted in the fallopian tube via a working channel of a hysteroscope inserted into the uterus via the cervix and positioned adjacent to the opening of the fallopian tube. Thus, it will be understood by those skilled in the art that the device 100 is preferably sized and shaped to fit within both the working channel of a device such as a hysteroscope and to pass through a body orifice such as the cervix.

The stent 102 may be substantially tubular or formed in any other shape corresponding to the shape of a portion of the lumen within which it is to be lodged. The stent 102 defines a channel 116 extending therethrough from the proximal end 112 to the distal end 114 and comprises a mesh structure 108 formed from one or more wire members 110. The wire members 110 may extend around an outer perimeter of the stent 102 in a zig-zag pattern alternating between proximal and distal peaks 118, 118'. For example, a stent 102 may include a plurality of zig zag wire members 110, each extending around a circumference of the stent 102 and arranged adjacent to one another along a length of the stent 102. Each of the wire members 110 is radially aligned adjacent wire members 102 so that proximal peaks 118 of one wire member 110 face distal peaks 118' of the of the wire member 110 immediately proximal thereto and distal peaks 118' of the wire member 110 face proximal peaks 118 of the wire member 110 immediately distal thereto. This facilitates the connection of these adjacent wire members 110 at the aligned proximal peaks 118 and distal peaks 118 by, for example, welding, soldering, adhesives or any other known connecting means. The connections between the peaks 118, 118' attach the series of wire members 110 to one another such that the wire members 110 together form the mesh structure 108. However, it will be understood by those of skill in the art that all or any desired portion of the peaks 118, 118' may be connected to one another to form a mesh structure 108 having a desired flexibility while maintaining a desired level of structural rigidity.

In one embodiment, the mesh structure 108 of the stent 102 includes Nitinol which, as understood by those skilled in the art, is an alloy having superelasticity and shape memory characteristics allowing the stent 102 to self-expand after implantation in the body lumen. For example, the mesh structure 108 may self-expand from a reduced diameter insertion configuration to an expanded, deployed configuration in which the stent 102 has a larger diameter (e.g., a diameter substantially equal to or slightly greater than an inner diameter of the lumen within which it is to be deployed. The stent 102 may typically expand to between 1.0 mm and 3.0 mm in the deployed configuration. The mesh structure 108 may be deformed into the reduced diameter insertion configuration and maintained below a critical temperature of the shape memory material (e.g., Nitinol) during preparation and insertion. The critical temperature may be selected to be below body temperature so that, as the stent 102 is elevated above this critical temperature through prolonged exposure to the temperature of the interior of the body, the mesh structure 108 reverts to a memorized shape (i.e., the deployed configuration) as would be understood by those skilled in the art. It will be understood by those of skill in the art, however, that the mesh structure 108 of the stent 102 may be formed of any known bio-compatible shape memory material.

The device 100 may comprise a basket structure 104 suspended across at least one of the proximal and distal ends 112, 114, respectively, of the channel 116. However, in a preferred embodiment, the device 100 comprises two basket structures 104 with one basket structure 104 suspended at each of the ends 112, 114. Each basket structure 104 includes at least one prong that is coupled to the stent 102 such that a surface of the basket substantially fills a cross-sectional area of the channel 116, providing a greater surface for tissue cells to grow. In a preferred embodiment, as best shown in FIG. 2, the basket structure 104 includes two prongs 122a, 122b, which are coupled to substantially diametrically opposed points of the stent 102 so that the basket structure 104 extends across the channel 116. The prongs 122a, 122b may be attached to the mesh structure 108 of the stent 102 using any known method such as welding, soldering and adhesives as would be understood by those of skill in the art.

It will be understood by those of skill in the art that the basket structure 104 may expand along with the stent 102 from the insertion configuration to the deployed configuration (e.g., as the prongs 122a, 122b are drawn apart through the expansion of the mesh structure 108 to which they are attached). Those skilled in the art will further understand that the stent 102 may be maintained in the reduced diameter insertion configuration by mechanically restricting its expansion (e.g., by maintaining it within the lumen of a delivery device) until it is in a desired position within the target lumen to be occluded. It will also be understood by those of skill in the art that any number of prongs of the basket structure 104 may be coupled to the stent 102 so long as the basket structure 104 extends across the channel 116 and thereby the body lumen once in the deployed configuration. For example, one prong of the basket structure 104 may be coupled to the stent 102, self-expanding along with the stent 102, to extend across the channel 116 of the stent 102.

The basket structure 104 includes cell growth promoter agent 106 in a center thereof such that after the device 100 has been implanted and expanded into the deployed configuration, benign cell growth will begin at the ends 112, 114, eventually occluding the fallopian tube. It will be understood by those of skill in the art, however, that the basket structure 104 may be formed of the cell growth promoting agent 106. Alternatively the cell growth promoting agent 106 may be incorporated in the structure of the basket structure 104. The basket structure 104 provides greater scaffolding and/or support of the body lumen while providing a greater inter-luminal surface area for promoting tissue growth both around and within the stent 102 of the device 100. The basket structure 104 bridges one side of the body lumen with the opposite side of the body lumen so that tissue may grow from each side of the body lumen to completely block the lumen.

The basket structure 104 may be formed of a metallic material such as Nitinol, copper or a bio-degradable magnesium. In an alternative embodiment, the basket structure 104 may be formed of a polymeric material such as PET, ePTFE or a super-absorbant material. The basket structure 104 may also include a shape memory or elastomer component such that deployment into the body may trigger the basket structure 104 to expand into a predetermined shape, which expands across the channel 116 and thereby the body lumen.

In a further embodiment, the basket structure 104 includes platinum coils making the device 100 visible after it has been deployed. The platinum coils may also be wrapped in polymer fibers or fibers of any other cell growth promoting agent 106, such as ultra high molecular weight polyethylene fibers, polyester fibers or copper fibers. In an alternative embodiment, the fibers of the cell growth promoting agents 106 may be treated with fibrous tissue growth promoting agents or sclerosing agents (e.g., silver salts PMMA, formaldehyde, alcohols, etc.) that are passively released after the device 100 has been implanted in a target lumen such as the fallopian tube. It will be understood by those of skill in the art that treatment may include, but is not limited to, injection, coating or plasma treatment of the fibers of the cell growth promoter agents 106 with the fibrous tissue growth agent. Fibrous tissue growth promoting agents and sclerosing agents may include any agents that increase the rate of scarring and encapsulation of the stent 102.

Figures 3A, 3B:
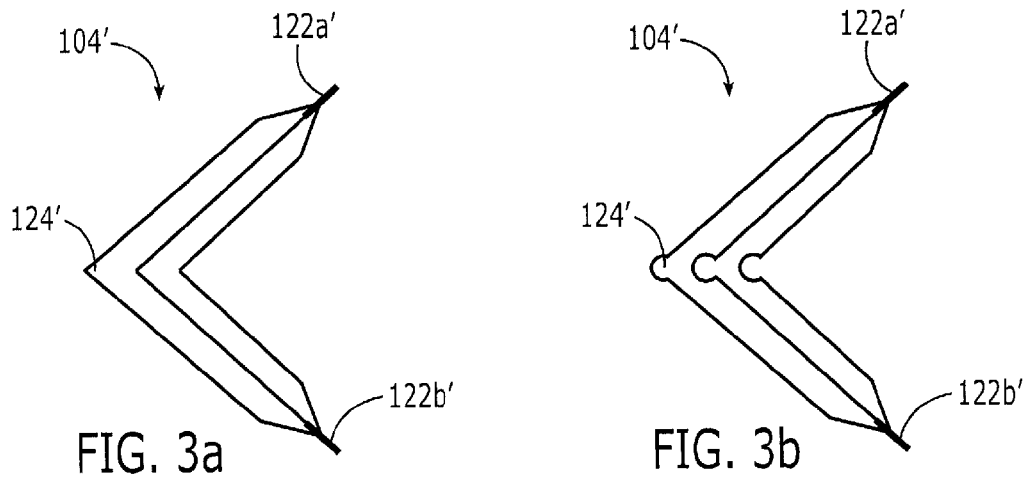
FIG. 3 shows a side view of a cell growth promoter agent in a balloon-like basket, according to another embodiment of the present invention.

In another embodiment, as shown in FIGS. 3a and 3b, a basket structure 104' may be substituted for the basket structure 104 in the device 100 described above. The basket structure 104', differs from the basket structure 104 in that the basket structure 104' is substantially balloon-like with a base of the basket structure 104' being non-planar and including a grooved or indented portion 124' holding the cell growth promoter agent 106'. The basket structure 104' also includes two ends 122a', 122b' that may be connected to the stent 102 (not shown) in substantially the same manner as described above in regard to device 100. Specifically, the balloon-like basket structure 104' may be attached to each of the ends 112, 114 of the stent 102 via any known attaching means. Similarly, the basket structure 104' includes cell growth promoter agents 106 (not shown) facilitating the growth of benign cells at the ends 112, 114 to occlude the target lumen (e.g., the fallopian tube).

Figure 4:
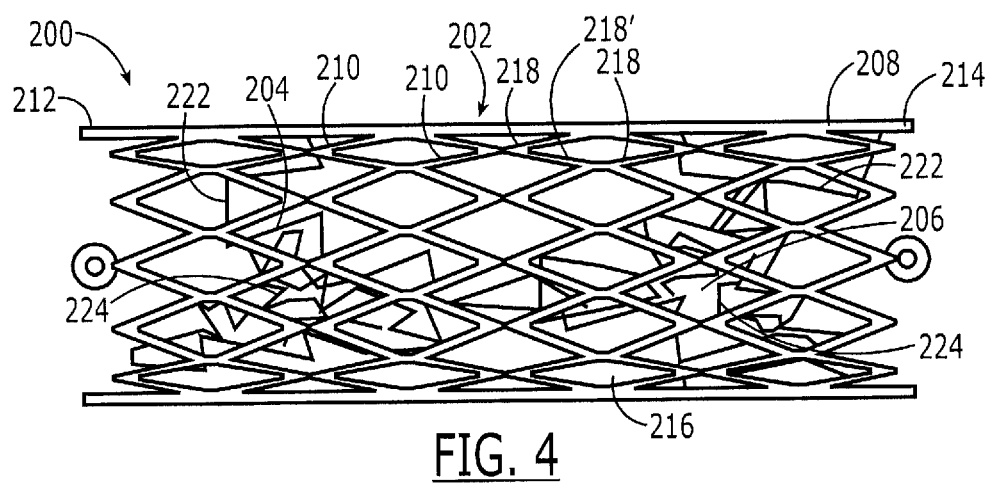
FIG. 4 shows a side view of a device, according to an alternative embodiment of the present invention, including a cell growth promoter agent basket that is integrated into an inner surface of the device.

As shown in FIG. 4, a device 200 according to a further embodiment of the invention comprises a stent 202 and a basket structure 204 including a cell growth promoter agent 206. The stent 202 may be substantially similar to the stent 102 as described above in regard to device 100. Specifically, the stent 202 may be comprised of a mesh structure 208 formed of a series of wire members 210 that may be connected, for example, via peaks 218, 218' of adjacent wire members 210. The stent 202 may also be substantially tubular extending from a proximal end 212 to a distal end 214 with a lumen 216 extending therethrough. The basket structure 204, however, differs from the device 100 in that it is integrated into the mesh structure 208 of the stent 202. Struts 222 of the basket structure 204 may be integrated into an inner surface of the stent 202 (i.e., by weaving the struts 222 through the mesh structure 208 such that the struts 222 extend across the lumen 216) to form holding pockets 224 for the cell growth promoter agent 206 (e.g., fibers bonded to the struts 222) to encourage tissue growth across the lumen 216 at each point at which such a holding pocket 224 is present.

It will be understood by those of skill in the art, however, that the basket structure 204 may also be formed of the cell growth promoting agent 206 or, in the alternative, the cell growth promoting agent 206 may be incorporated into a structure of the basket structure 204. In a preferred embodiment, the basket structure 204 may be formed of copper such that the copper material mechanically irritates the tissue to create scarring tissue and occlusion. Similarly to the basket structure 104, the basket structure 204 may include platinum coils to facilitate visualization of the device 200 after deployment. As would be understood by those skilled in the art, the cell growth promoter agent 206 may be treated with fibrous tissue growth promoting agents or sclerosing agents.

It will be understood by those of skill in the art that various modifications can be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. A device for occluding a target body lumen, comprising:
   a wire structure defining a wire structure lumen extending therethrough and movable between a reduced diameter insertion configuration and an expanded diameter deployed configuration; and
   a basket structure extending across the wire structure lumen and including therein a cell growth promoting agent to promote cell growth across the wire structure lumen to occlude the target body lumen,
   wherein the basket structure is formed on an inner surface of the wire structure and includes struts that are interwoven with the wire structure to form pockets that hold the cell growth promoting agent.

2. The device of claim 1, wherein the basket structure is attached to substantially diametrically opposed portions of the wire structure across one of a proximal and a distal end of the wire structure lumen.

3. The device of claim 1, wherein the basket structure is formed of the cell growth promoting agent.

4. The device of claim 1, wherein the basket structure is attached to at least one portion of the wire structure, the basket structure expanding to extend across the wire structure lumen.

5. The device of claim 1, wherein the wire structure is formed from a series of wire members, each wire member extending around an outer perimeter of the device, wherein portions of the adjacent wire members are connected to one another.

6. The device of claim 5, wherein the basket structure includes four prongs such that the basket structure is attached to the wire member by two of the prongs on opposite sides thereof.

7. The device of claim 1, wherein the basket structure is attached to the wire structure via one of welding, soldering or an adhesive.

8. The device of claim 1, wherein the basket structure is balloon-shaped and attached to the wire structure via two prongs.

9. The device of claim 1, wherein the basket structure includes platinum coils for visibility during deployment.

10. The device of claim 9, wherein the platinum coils are wrapped in fibers of the cell growth promoting agent.

11. The device of claim 1, wherein the cell growth promoting agent is one of ultra high molecular weight polyethylene fibers, polyester fibers, copper fibers, copper barbs, collagen fibers and a porous polymer.

12. The device of claim 11, wherein the cell growth promoting agent is plasma treated.

13. The device of claim 1, wherein fibers of the cell growth promoting agent is treated with a fibrous tissue growth promoting agent that increases scarring and encapsulation.

14. The device of claim 13, wherein the fibrous tissue growth promoting agent is one of silver salts PMMA, formaldehyde and alcohol.

15. The device of claim 1, wherein the wire structure consists of Nitinol such that the wire structure self-expands in the deployed configuration when triggered by a threshold value of heat within the body.

16. The device of claim 1, wherein the basket structure consists of one of a metallic material, a polymeric material and a super-absorbent material.

17. A method for occluding a target body lumen, comprising:
   inserting to a target site within the body lumen a wire structure defining a wire structure lumen extending therethrough while maintaining the wire structure in a reduced diameter insertion configuration, the wire structure including a basket structure extending across the wire structure lumen and including therein a cell growth promoting agent to promote cell growth across the wire structure lumen to occlude the body lumen, wherein the basket structure is formed on an inner surface of the wire structure and includes struts that are interwoven with the wire structure to form pockets that hold the cell growth promoting agent; and
   expanding the wire structure to an expanded diameter deployed configuration in which the wire structure engages the wall of the body lumen.

18. The method of claim 17, wherein the body lumen is a fallopian tube.

* * * * *